July 5, 1966 H. C. SWIM ETAL Plant Pat. 2,655
ROSE PLANT
Filed June 22, 1965
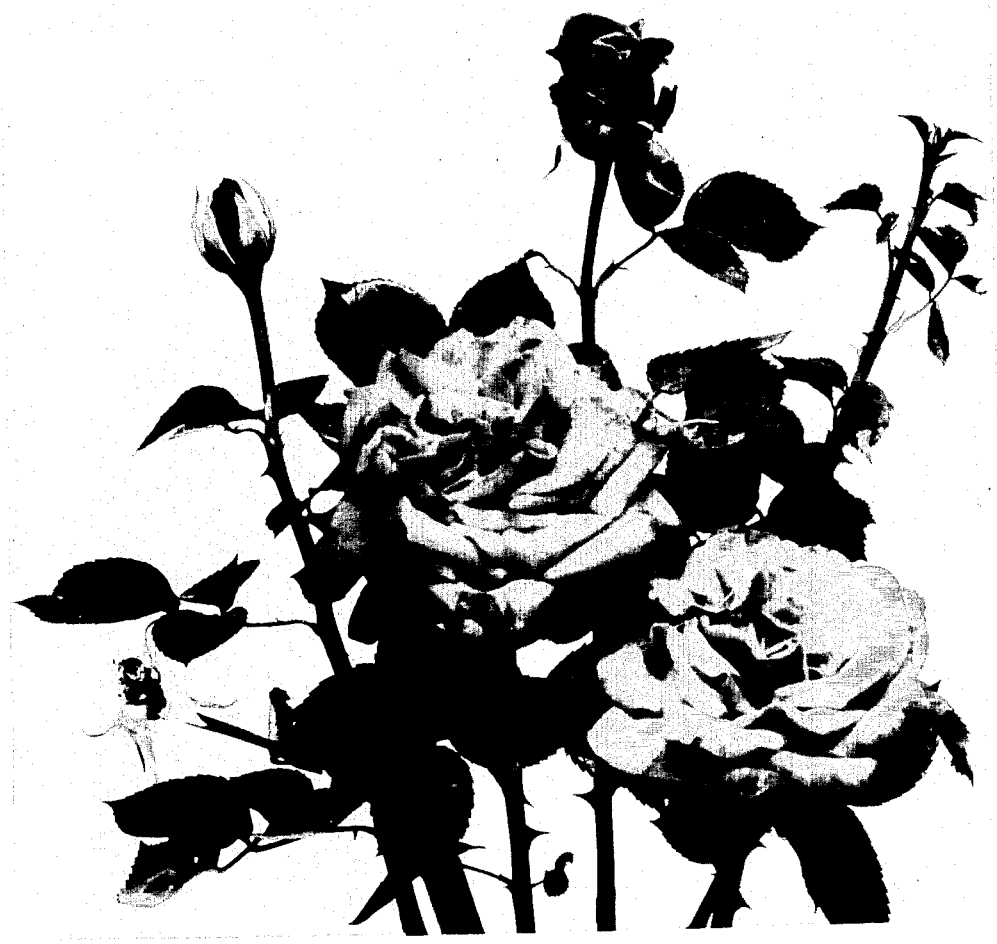
Inventors.
H. C. Swim and
O. L. Weeks
By: Robb & Robb
Attorneys.

United States Patent Office

Plant Pat. 2,655
Patented July 5, 1966

2,655
ROSE PLANT

Herbert C. Swim, 1329 College Way, Ontario, Calif., and O. L. Weeks, 4759 Philadelphia, Chino, Calif.

Filed June 22, 1965, Ser. No. 466,139
1 Claim. (Cl. Plt.—21)

The present invention relates to a new and distinct variety of rose plant of the hybrid tea class, which was originated by us by crossing an unnamed and unpatented seedling of "World's Fair" (Plant Patent No. 362) × "Chrysler Imperial" (Plant Patent No. 1,167) with the variety "Happiness" (Plant Patent No. 911).

As the result of this breeding, we have produced a new rose variety having the following unique combination of characteristics which are outstanding therein and which distinguish it from its parents, as well as from all other varieties of which we are aware:

(1) A relatively very tall plant habit, with attendant long flower stems;

(2) Leaves composed of relatively round and flat leaflets of medium to large size;

(3) Long-pointed to urn-shaped flower buds as they begin to unfold;

(4) A heavy leathery petal texture or substance, with attendant long-lasting qualities of the petals and flowers;

(5) A very dark red to near black color of the flower buds as they begin to open, with the open flowers having very dark red to black outer petals and bright red petals in the central portion of the flowers;

(6) Relative freedom from blue color or blue-related pigment in the general color effect of the three-day open flowers and also in the flowers at the end of their useful life; and (7) A pleasing and strong flower fragrance corresponding to a combination of spicy fragrance and damask.

In comparison with its unnamed seed parent, our new variety has flower stems which are substantially longer than average, as distinguished from the average length of the flower stems of this parent; the flower buds are long-pointed to urn-shaped instead of short-pointed to ovoid as the flower buds of the parent variety begin to unfold; the flower buds are very dark red and nearly black at the stage when they begin to unfold, instead of being fairly uniformly dark red, similar to the variety "Chrysler Imperial," in the case of the seed parent; the open flowers of the new variety are characterized by having very dark red outer petals and very bright red central petals instead of the more uniformly dark red petals throughout the flower of the seed parent; and the new variety has petals of unusually hard and leathery substance, as distinguished from the medium soft petal texture and substance of the parent variety, thus giving the petals and flowers of the new variety a much longer lasting quality.

As compared with its pollen parent "Happiness," the new variety has leaflets that are substantially more round and flat than those of this parent; fewer large and small prickles than the parent variety; a very dark red and nearly black at times bud color, with the color maintaining a very dark red coloration in the outer petals and a very bright red color in the central portion of the open flowers, instead of the fairly uniform dark red flower color of the parent variety; and a strong, spicy and damask fragrance as distinguished from the little or no flower fragrance of the parent variety.

Asexual reproduction of our new variety of budding as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Tall; bush; outdoor; seedling; for cut flowers and for garden decoration.

Class: Hybrid tea.

Breeding: Seedling.

*Seed parent.*—An unnamed seeling of "World's Fair" × "Chrysler Imperial."

*Pollen parent.*—"Happiness."

Propagation: Holds its distinguishing characteristics through succeeding propagations by budding.

*Flower*

Locality where grown and observed: Chino, California.

Flowers borne: Singly; on long and strong stems.

Quantity of bloom: Free, outdoors.

Continuity: More or less continuous during growing season.

Fragrance: Strong. Nature—combined spicy and damask.

Bud:

*Peduncle.*—From short to medium length; medium heavy caliper; erect; smooth, except for few scattered stipitate glands. Color—yellowish green, overlaid heavily with reddish-purple.

*Before calyx breaks.*—Size—from medium to large. Form—medium length; pointed; with foliaceous appendages on the surface of the bud; often with foliaceous parts extending beyond the tip of the bud equal to ¼ to ½ or more of its length. Color—Dark Red, Plate 2.5R 3/7, overlaid with black to Moderate Red, Plate 2.5R 4/10, except for small spot of greenish-white at base.

*As calyx breaks.*—Color—Dark Red, Plate 2.5R 3/7, overlaid with varying amounts of black.

*As first petal opens.*—Size—medium for its class. Form—from long-pointed to urn-shaped. Color: Outside—Dark Red, Plate 2.5R 3/7 at or near base, but with progressively greater intensity or black overlay approaching the apex of the petals, with the intensity being in direct proportion to earliness of exposure to light; inside—small spot at attachment of Brilliant Greenish-Yellow, Plate 7.5Y 9/8, with remainder of petal seeming basically from Dark Red, Plate 2.5R 3/7 to Moderate Red, Plate 2.5R 4/10, but all except a small part near base being so intense or overlaid with black that basic color is obscured and is progressively more intense toward apex.

*Opening.*—Opens up well.

Bloom:

*Size (when fully open).*—From medium to large; from 4½ inches to 5 inches.

*Petalage.*—Double; from 30 to 45 petals, plus 4 to 10 petaloids; arranged more or less regularly.

*Form.*—High-centered at first and remaining relatively high-centered; petals being at first loosely rolled outward and remaining loosely rolled outward at maturity.

Petals:

*Texture.*—Very thick; leathery.

*Appearance.*—Inside—velvety. Outside—from satiny to velvety.

*Shape.*—Outside—very broadly oval; slightly and irregularly scalloped; apex irregularly notched. Intermediate—broadly obovate, with apex having 1 or 2 notches. Inside—generally obovate; occasionally irregularly scalloped, and apex having 1 or 2 notches; sometimes one or both margins being slightly wrinkled.

This description of a newly opened flower was made from a rose grown outdoors during the month of May at Chino, California:

*Color.*—Outer petal: Outside surface—except for small spot at point of attachment of Brilliant Greenish-Yellow, Plate 7.5Y 9/8, basic color is near Moderate Red, Plate 2.5R 4/10, but overlaid with from Dark Red, Plate 2.5R 3/7 to black in varying intensities; inside surface—most with vegetative streaks in general area of the midrib devoid of color overlay, but basic color being covered with tomentum, said basic color being near Moderate Red, Plate 2.5R 4/10, with remainder of petal having overlay of from Dark Red, Plate 2.5R 3/7 to black which becomes progressively more intense toward apex and upper margin. Intermediate petal: Outside surface—basic color near Moderate Red, Plate 2.5R 4/10, with somewhat variable overlay of Dark Red, Plate 2.5R 3/7, said overlay being generally more intense in upper part of petal and at margins; inside surface—basic color near Moderate Red, Plate 2.5R 4/10, but modified by some yellow and variably by overlay of Dark Red, Plate 2.5R 3/7, with apex being near black at times. Inner petal: Outside surface—rather uniformly between Moderate Red, Plate 2.5R 4/10 and Dark Red, Plate 2.5R 3/7; inside surface—basic color near Moderate Red, Plate 2.5R 4/10, influenced a bit by yellow and overlaid in a slightly streaked pattern between veins with Dark Red, Plate 2.5R 3/7.

This description was made from a rose that was open for three days outdoors during the month of May at Chino, California:

*Color.*—Outer petal: Outside surface—except for small yellowish-white spot at point of attachment, basic color is near Moderate Red, Plate 2.5R 4/10, overlayed in varying degree with from Dark Red, Plate 2.5R 3/7 to black, especially over upper half of petal; inside surface—very small area at point of attachment is yellowish-white, abruptly changing to somewhat larger area of Strong Purplish-Red, Plate 7.5RP 4/11, which in turn changes rapidly to the basic color of Moderate Red, Plate 2.5R 4/10, overlaid by from Dark Red, Plate 2.5R 3/7 to black. Inner petal: Outside surface—yellowish white spot at point of attachment, with lower portion of petal near Strong Purplish-Red, Plate 10RP 4/12, changing gradually on upper portion to a shade between Strong Purplish-Red, Plate 10RP 4/12 and Moderate Red, Plate 2.4R 4/10. Inside surface—yellowish-white at point of attachment, with adjacent small area near Strong Purplish-Red, Plate 10RP 4/12, progressing rapidly toward apex to more orange red shades, faintly at first but with greater intensity at upper margin.

*General color effect.*—Newly opened flower—outer portions of flower are very dark red, often near black, while central portion is between Strong Red, Plate 5R 4/12 and Moderate Red, Plate 2.5R 4/10, overlaid with Dark Red, Plate 2.5R 3/7 at apex of petals.

*General color effect.*—Three-days open—outer portions of flower are very dark red, often appearing overlaid with black, while center of flowers is basically Moderate Red, Plate 2.5R 4/10, but with some overlay of Dark Red, Plate 2.5R 3/7.

*Behavior.*—Drop off cleanly, except for a few petals and petaloids, but flowers last in good condition for a relatively long time.

*Flower longevity.*—On bush outdoors—10 days in May. Cut roses grown outdoors and kept at living room temperatures—7 days in May.

*Reproductive organs*

Stamens: Many; irregularly arranged about pistils; mixed with petaloids to some extent.

Filaments: Medium length; most with anthers. Color—reddish.

Anthers: Medium size; all open at once, more or less. Color—whitish-yellow, with golden valves.

Pollen: Abundant. Color—gold.

Pistils: Medium quantity.

Styles: Uneven; from short to medium length; medium caliper; bunched in slightly twisted fashion.

Stigma: Pinkish-white color.

Ovaries: Some enclosed in, but many protruding from, calyx.

Hips: Flat at top; usually cupped or vaseshaped; walls thick and fleshy. Color—yellow and russet.

Sepals: Permanent; moderately short; from straight to spear-shaped or curled.

Seeds: Many; medium size for class.

*Plant*

Foliage:

*Leaves.*—Compound of 5 to 7 leaflets; normal quantity; from medium size to large; moderately heavy; non-glossy.

*Leaflets.*—Shape—nearly round. Apex—from acute to acuminate. Base—generally round. Margin—simply serrate.

*Color.*—Mature: Upper surface—normal green; under surface—light yellowish-grey green. Young: Upper surface—yellowish-green, with reddish-purple overlay, especially at margins; under surface—yellowish-green, with reddish-purple veins and midrib.

*Rachis (the supporting stem of the compound leaf).*—Medium weight. Upper side—grooved; ridges sparsely glandular. Under side—prickly; with 4 or 5 hooked prickles.

*Stipules.*—Medium length; moderately narrow; with short points turning out at an angle of approximately 45°.

*Disease resistance.*—Average resistance to mildew, as compared with other red flowered hybrid tea varieties grown under comparable cultural conditions at Chino, California.

Growth:

*Habit.*—Tall; upright; moderately branched.

*Growth.*—Very vigorous.

*Canes.*—Moderately heavy caliper.

*Main stems.*—Color—brownish red. Large prickles—several; medium length; from straight to slightly hooked downward; with short broad base; color—greyish brown. Small prickles—few; color—grey-brown. Hairs—none.

*Branches.*—Color—reddish-green. Large prickles—several; medium length; from straight to slightly hooked downward; with short broad base; color—brown. Small prickles — few; color — brown. Hairs—none.

*New shoots.*—Color—reddish-purple. Large prickles—several; medium length; from straight slightly hooked downward; with short broad base; color—reddish-purple. Small prickles—few; color—reddish-purple. Hairs—none.

We claim:

A new and distinct variety of rose plant of the hybrid tea class, substantially as herein shown and described, characterized particularly as to novelty by the unique combination of a relatively very tall plant habit, with attendant long flower stems, leaves composed of relatively round and flat leaflets of medium to large size, long-pointed to urn-shaped flower buds as they begin to unfold, a heavy, leathery petal texture or substance, with attendant long-lasting qualities of the petals and flowers, a very dark red to near black color of the flower buds as they begin to open, with the open flowers having very dark red to black outer petals and bright red petals in the central portion of the flowers, relative freedom from blue color or blue-related pigment in the general color effect of the three-day open flowers and also in the flowers at the end of their useful life, and a pleasing and strong flower fragrance corresponding to a combination of spicy fragrance and damask.

No references cited.

ANTONIO F. GUIDA, *Acting Primary Examiner.*

R. E. BAGWILL, *Assistant Examiner.*